(12) United States Patent
Sardo

(10) Patent No.: US 8,791,051 B2
(45) Date of Patent: *Jul. 29, 2014

(54) SOLUTIONS OF CIPC AND OF A TERPENE OR OF A TERPENE OIL AND THEIR USES FOR THE ANTIGERMINATIVE TREATMENT OF BULBS OR TUBERS

(75) Inventor: Alberto Sardo, Chateaurenard (FR)

(73) Assignee: Xeda International, Saint Andiol (FR)

( * ) Notice: Subject to any disclaimer, the term of this patent is extended or adjusted under 35 U.S.C. 154(b) by 1335 days.

This patent is subject to a terminal disclaimer.

(21) Appl. No.: 10/967,137

(22) Filed: Oct. 19, 2004

(65) Prior Publication Data

US 2005/0137090 A1    Jun. 23, 2005

(30) Foreign Application Priority Data

Dec. 18, 2003   (FR) ...................... 03 14908

(51) Int. Cl.
- *A01N 47/20* (2006.01)
- *A01N 65/28* (2009.01)
- *A01N 25/02* (2006.01)
- *A01N 25/30* (2006.01)

(52) U.S. Cl.
USPC ........... 504/143; 504/118; 504/174; 504/182; 504/183; 504/300; 504/362

(58) Field of Classification Search
None
See application file for complete search history.

(56) References Cited

U.S. PATENT DOCUMENTS

| 5,811,372 A * | 9/1998 | Riggle et al. ................. 504/138 |
| 6,723,364 B1 * | 4/2004 | Bompeix et al. .............. 426/320 |
| 8,207,090 B2 * | 6/2012 | Sardo ......................... 504/116.1 |

FOREIGN PATENT DOCUMENTS

| FR | 2 778 065 | 11/1999 |
| WO | 00/32054 | 6/2000 |

OTHER PUBLICATIONS

Kleinkopf et al., Sprout Inhibition in Storage:Current Status, New Chemistries and Natural Compounds, American Journal of Potato Research, 2003, http://findarticles.com/p/articles/mi_qa4069/is_200309/ai_n9259326/print.*
Kleinkopf et al., Sprout Inhibition in Storage:Current Status, New Chemistries and Natural Compounds, American Journal of Potato Research, 2003, 80:317-327.*
Kleinkopf et al. (Sprout Inhibition in Storage:Current Status, New Chemistries and Natural Compounds, American Journal of Potato Research, 2003, 80:317-327).*

* cited by examiner

*Primary Examiner* — Abigail Fisher
*Assistant Examiner* — Frank Choi
(74) *Attorney, Agent, or Firm* — B. Aaron Schulman, Esq.; Stites & Harbison, PLLC.

(57) ABSTRACT

The present invention relates to solutions of CIPC and of one or more terpenes or terpene oils for the antigerminative treatment of bulbs and tubers. This use is particularly appropriate for the treatment of potato tubers. The CIPC solution contains from 50 to 80% by weight of CIPC relative to the total volume of the solution. Examples of the terpenes and terpene oils are eugenol, isoeugenol, clove oil and their salts and mixtures thereof.

15 Claims, No Drawings

SOLUTIONS OF CIPC AND OF A TERPENE OR OF A TERPENE OIL AND THEIR USES FOR THE ANTIGERMINATIVE TREATMENT OF BULBS OR TUBERS

The present invention relates to solutions of CIPC and of one or more terpenes or terpene oils for the antigerminative treatment of bulbs and tubers. This use is particularly appropriate for the treatment of potato tubers.

After harvesting potatoes or other tubers, they are stored at temperatures of the order of 20° to 30° C. for about ten days in order to harden their peridermal layer (or "skin"), and then gradually cooled down to their storage temperature which is about 10° C.

During the first and second months following their harvest the tubers remain in the resting state and show little tendency toward germination.

However, before the end of this period, the tubers must be chemically treated in order to inhibit germination which would be responsible for harmful effects, such as a loss of weight, storage of starch as sugar and a decrease in the quality of the tubers and a deterioration of their appearance. In addition, the eyes and the surrounding tissues contain high levels of toxic glycoalkaloids which are not destroyed during cooking.

The methods of antigerminative treatment which are most widely used involve chemical agents such as chloropropham, also called chlorpropham, CIPC or isopropyl (3-chlorophenyl)carbamate. In general, CIPC is applied to stored tubers by means of thermonebulization techniques. In general, thermonebulization involves the application of CIPC by means of a hot air stream in order to produce an aerosol.

According to a first practice, the thermonebulization is carried out using pure CIPC. However, this technique results in unsatisfactory application of the pure active ingredient to the tubers. Indeed, CIPC has a tendency to form lumps and/or not to become evenly distributed on the tubers.

According to another practice, CIPC is formulated in a solvent medium, such as methylene chloride or methyl alcohol. Here again, this technique does not give satisfactory results since the solvents normally used have low boiling points and tend to evaporate rapidly during thermonebulization. This results in the application of pure active ingredient having the same disadvantages as the preceding technique.

Attempts have been made to apply CIPC with pure terpene compounds. However, during these attempts, CIPC and the terpene compound are successively applied to the potatoes treated. The abovementioned difficulties of distributing CIPC on tubers therefore remain.

Moreover, CIPC is sparingly soluble in conventional solvents, and maximum CIPC concentrations of the order of 30% (weight/volume) are generally obtained. At best, concentrations of the order of about 54% at 180° C. have been obtained. This low solubility therefore implies the use of large quantities of solvent and/or of formulation in order to obtain the required quantities of active formula. Now, it is sought in general to limit the use of these solvents because of their own toxicity and/or of the danger involved in using them, in particular because of their low boiling points which cause high risks of inflammability.

The use of synthetic derivatives for application to fruits and vegetables during their growth and storage is limited. In particular, the levels of CIPC have been the subject of increasingly severe regulations. Consequently, while CIPC is used to limit the formation of eyes on tubers, its toxicity could call into question its use at the usual doses. Consequently, efforts are being made to limit to a minimum the quantity of CIPC to be applied to bulbs and tubers.

Finally, the available CIPC formulations have poor stability, especially at low temperature, which makes them unsuitable for storage, especially in cold rooms for storing bulbs and/or tubers.

It has now been discovered, and that is one of the subjects of the present invention, that terpenes and/or terpene oils have a high CIPC-dissolving power. In particular, the use of such terpenes and/or terpene oils makes it possible to obtain clear CIPC solutions and to reach CIPC concentrations greater than 50% by weight of CIPC relative to the total volume of the solution, at room temperature, or even temperatures as low as 0° C. Consequently, the formulations of the present invention make it possible to limit the quantity of formulated product to be used.

Moreover, the solutions according to the invention use terpenes or terpene oils at high boiling temperature, preferably greater than 230° C., more preferably still greater than 240° C. Thus, this high boiling temperature makes it possible to carry out the thermonebulization at higher temperature, providing better fog and therefore better distribution on the bulbs and/or tubers treated. Also, the terpene compound or the oil is not degraded or is hardly degraded and/or forms fog of good quality during thermonebulization, thus allowing better distribution on the tuber treated.

Moreover, these high boiling points thus make it possible to reduce the risk of inflammability compared with the conventional solvents generally used in CIPC formulations where the solvents would be completely vaporized.

Moreover, the solutions according to the invention are perfectly stable up to several months, preferably at least one month, at low temperature, preferably down to 0° C. This therefore allows users to store CIPC formulations in cold rooms.

Terpenes and/or terpene oils have an inherent biocidal activity against fungi and bacteria which attack potatoes. They therefore make it possible to improve the properties of CIPC formulations.

Finally, the combination of said terpenes and/or terpene oils with CIPC can potentiate the antigerminative effect of the formulations.

According to a first subject, the present invention relates to CIPC solutions containing one or more terpenes and/or terpene oils.

According to a preferred aspect, said solutions contain from 50 to 80% by weight of CIPC, preferably 60 to 70%, more preferably still 62 to 65%.

According to another preferred aspect, said solutions contain from 30 to 60% by weight of terpenes and/or terpene oils, preferably between 30 and 40% by weight.

According to another preferred aspect, said solutions of the invention also contain one or more emulsifiers, more preferably a nonionic emulsifier. Generally, said solutions contain from 0 to 20% by weight of emulsifier.

In the preceding text and in the text which follows, the percentages are by weight/volume relative to the total volume of the composition.

According to another subject, the present invention also relates to the method for treating bulbs or tubers, in particular potatoes, using the solution according to the invention, more preferably the antigerminative and/or biocidal treatment.

According to another subject, the present invention also relates to the use of a terpene and/or terpene oil for solubilizing CIPC.

According to another subject, the present application also relates to the method for preparing CIPC formulations, comprising the step consisting in solubilizing CIPC in the presence of a terpene and/or terpene oil.

According to the present invention, the expression "terpene" is understood to mean the compounds present in the essential oils derived from plants, such as limonene, eucalyptol, safrole, terpineol, L- or D-carvone, eugenol, isoeugenol, menthol, preferably safrole, terpineol, eugenol, isoeugenol, menthol. Eugenol is more particularly preferred.

According to the invention, the expression "terpene oil" is understood to mean the natural oils from which terpenes are extracted. These oils include in particular caraway oil, clove oil, eucalyptus oil, common mint oil, peppermint oil, citronnella oil, preferably common mint oil, peppermint oil and clove oil. Clove oil is more particularly preferred.

The terpenes according to the invention also comprise the salts of terpenes and/or mixtures thereof. Particularly preferred salts are in particular the alkali metal salts, such as the sodium salts, the lithium salts and the potassium salts.

According to a particularly preferred embodiment, the terpene is in the form of a dietarily acceptable salt or mixture of salts. In this case, a lower volatility of the terpene is indeed observed. In this way, the duration of protection of the tubers and bulbs after application of the solution according to the invention is prolonged.

According to the present invention, the expression "emulsifier" is understood to mean any type of agent normally used to this effect, such as ethoxylated fatty alcohols, ethoxylated fatty acids, ethoxylated alkylphenols or any other nonionic product.

The solution according to the invention may be applied to the tubers and bulbs using any of the methods known in the art, in particular by brushing, dipping, sprinkling, spraying, showering or thermonebulization. Preferably, the solution is applied by thermonebulization, at a temperature of between 230 and 250° C. This technique is known per se.

The application may be continuous or intermittent during the period of storage.

Preferably, the application is repeated in the storage chamber every two months approximately.

Of course, it is possible to add to the composition according to the invention one or more agents for reducing evaporation of the active ingredient. Such agents are known in the art and may be chosen in particular from water-dispersible polyterpenes, glycerol esters of pine resin, gum lac, lecithins, drying oils, polyvinyl alcohol, polyvinylpyrrolidone, alkali metal polyacrylates, gum arabic.

The composition may additionally contain various surfactants known per se.

The final formulation of the solution according to the invention may depend on the method used for its application to the bulbs and tubers and on the nature of the products treated. It may be prepared by methods known per se.

The solution according to the invention is prepared in a conventional manner by solubilizing CIPC in the presence of a terpene or a terpene oil, optionally with stirring.

When the treatment composition comprises a dietarily acceptable salt, it may be introduced into the composition during its preparation in the form of a salt or in a neutral form. In this latter case, the salt is formed in situ by adding an appropriate base, such as an alkali metal hydroxide (sodium hydroxide or potassium hydroxide).

The quantity of solution according to the invention which should be applied to the tubers and bulbs essentially depends on the method of application selected. In general, there are applied in total, over a period of 6 months, from 20 to 30 g, preferably from 25 to 28 g of CIPC per ton of bulbs or tubers treated. More generally, the quantity of active ingredient applied is adjusted according to the duration of storage.

The following examples are given by way of nonlimiting illustration of the present invention.

EXAMPLE 1

A solution according to the invention was prepared in the following manner:

60 g of CIPC (marketed by Luxan Holland) were added to 36 g of eugenol (marketed by Charabot). The mixture is stirred until a clear solution is obtained. As emulsifier, 11 moles of ethoxylated lauryl alcohol were added at a concentration of 4 g per 100 g. The solution obtained has a concentration of 636 g/l of CIPC and 380 g/l or eugenol.

By way of comparison, a customarily used solution of CIPC in methylene chloride has a concentration of 30% by weight/volume.

EXAMPLE 2

The efficacy of the solutions according to the invention and the prior art CIPC compositions in the antigerminative treatment of potato tubers was evaluated in the following manner.

A. Solution of Example 1 at 636 g of CIPC

The applications are carried out by thermonebulization at 240° C. with the aid of Electrofog XEDA. For each score, samples in net bags are placed at the center of cases among the filling tubers so as to be extracted therefrom at the desired dates for the purpose of analysis.

B. Formulation Containing 200 g/l of CIPC in a Mixture of Water-Soluble Solvents, Water and Organic Wetting Agents The applications of the formulation are carried out by thermo-nebulization at 180° C. with the aid of an electrical apparatus (Electrofog XEDA) with a first application 15 days to 3 weeks after filling the cell. For each date, the tuber samples, placed in individual net bags, are embedded in cases homogeneously distributed in the storage cell. At the chosen date, they are extracted and scored.

C. CIPC in Powdered Form (1%)

For each scoring date, the application is carried out individually on samples of at least 50 tubers suitably weighed and placed in kraft paper bags. The dusting is carried out at the surface of the tubers placed in the bag which is then closed and shaken. They are placed in bulk bins of the VCP cell kept at the set temperature so as to be taken out at the desired date. The dose selected for the efficacy trials is 5 ppm per storage period of 3 months.

D. Untreated Control

For each scoring date, untreated tuber samples are placed in kraft paper bags placed in quite separate bulk bins and stored in the VCP cell. This cell is operated at the same set temperature and the cases are kept therein during the entire period of storage and are then removed for the scorings at the desired date.

The conditions for applying the formulations A, B, C, D are summarized in the following table 1.

TABLE 1

Efficacy trials at 6 months - products and doses applied

| Condition | Active ingredient | Concentration | Dose | Active ingredient dose | Application technique | Dates of application | Experimental conditions T° of the pile | Germination state |
|---|---|---|---|---|---|---|---|---|
| A | CIPC | 636 g/l | 19 ml/t then 13 ml/t then 13 ml/t | 12 ppm then 8 ppm then 8 ppm | Thermonebulization at 240° C. 15 d to 20 d after placing in storage and then every 6 to 8 weeks | 1st treatment on 11/09 2nd treatment on 12/22 3rd treatment on 2/02 | 8° C. 7.4° C. 7.5° C. | Beginning white point eyes <2 mm |
| B | CIPC | 200 g/l | Total = 45 ml/t 60 ml/t then 40 ml/t then 30 ml/t | Total = 28 ppm 12 ppm then 8 ppm then 6 ppm | Thermonebulization at 180° C. 15 d to 20 d after placing in storage and then every 6 to 8 weeks | 1st treatment on 11/09 2nd treatment on 12/27 3rd treatment on 02/21 | 8.3° C. 7.6° C. 7.7° C. | Beginning white point white point |
| C D | CIPC | 1% | Total = 130 ml/t 1.0 kg/t | Total = 26 ppm 10 ppm | Dusting during bagging | on 10/20 | | |

The results on the Bintje and Nicola varieties are summarized in the following tables 2 and 3.

TABLE 2

Antigerminative efficacy at 6 months - Bintje variety

| Specialty | Abs/eyes | White point | <2 mm | 2-5 mm | >5 mm | >2 mm | Germination index | Weight eyes | Weight loss |
|---|---|---|---|---|---|---|---|---|---|
| A | 3.3 | 82.2 | 9.0 | 4.1 | 1.4 | 5.5 | 9.7 | 0.7 | 3.7 |
| B | 3.1 | 83.9 | 7.0 | 3.6 | 2.5 | 6.1 | 10.4 | 0.7 | 5.2 |
| C | 0.0 | 46.8 | 31.3 | 11.1 | 10.8 | 21.9 | 22.6 | 19.9 | 6.5 |
| D | 0.0 | 8.0 | 26.5 | 28.3 | 37.2 | 65.5 | 52.6 | 39.9 | 6.5 |
| Significance | HS | HS | HS | HS | HS | HS | HS | S | HS |
| C.V. (as %) | 124.5 | 18.6 | 57.1 | 37.6 | 114.5 | 65.0 | 56.9 | 156.6 | 8.8 |

TABLE 3

Antigerminative efficacy at 6 months - Nicola variety

| Specialty | Abs/eyes | White point | <2 mm | 2-5 mm | >5 mm | >2 mm | Germination index | Weight eyes | Weight loss |
|---|---|---|---|---|---|---|---|---|---|
| A | 5.6 | 75.9 | 11.7 | 5.2 | 1.6 | 6.84 | 10.3 | 0.1 | 5.7 |
| B | 1.7 | 73.7 | 19.5 | 3.6 | 1.5 | 5.05 | 10.4 | 0.4 | 6.5 c |
| C | 0.3 | 44.4 | 39.2 | 7.5 | 8.6 | 16.14 | 19.8 | 12.3 | 8.3 |
| D | 0.0 | 3.1 | 13.8 | 19.7 | 63.4 | 83.14 | 73.4 | 122.1 | 8.9 |
| Significance | HS | HS | HS | HS | HS | HS | HS | HS | HS |
| C.V. (as %) | 41.1 | 15.0 | 42.0 | 48.5 | 37.5 | 26.5 | 21.3 | 94.6 | 5.9 |

HS: highly significant;
S: significant;
C.V.: coefficient of variation.

These results show that the solutions according to the invention make it possible to obtain comparable results while greatly reducing the quantity of product applied.

EXAMPLE 3

The stability of the solutions of the invention and of the compositions of the prior art has been studied.

The solution of example 1 containing 63.6% (weight/volume) of CIPC was kept at 0° C. for one month. The solution remained perfectly clear.

A formulation containing 25% of CIPC in a mixture of water-soluble organic solvents, water and wetting agents stored at 0° C. for one month is cloudy and has crystals.

The invention claimed is:

1. A CIPC solution comprising from 40 to 80% by weight of the CIPC, and from 20 to 60% by weight of clove oil, relative to the total volume of the solution.

2. The solution according to claim 1, comprising from 60 to 70% by weight of the CIPC, relative to the total volume of the solution.

3. The solution according to claim 1, comprising from 30 to 40% by weight of clove oil, relative to the total volume of the solution.

4. The solution according to claim 1, further comprising one or more emulsifiers.

5. The solution according to claim 1, further comprising a nonionic emulsifier.

6. The solution according to claim 1, further comprising from 0 to 20% by weight of an emulsifier.

7. A method for treating bulbs or tubers, wherein the solution as claimed in claim 1 is applied to the bulbs or tubers.

8. The method as claimed in claim 7, for the antigerminative treatment of potatoes.

9. The method as claimed in claim 7, wherein said solution is applied by thermonebulization.

10. The method as claimed in claim 7, wherein the solution is applied at a temperature of between 230 and 250° C.

11. A method for treating bulbs or tubers, wherein the solution as claimed in claim 3 is applied to the bulbs or tubers.

12. The method as claimed in claim 11, for the antigerminative treatment of potatoes.

13. The method as claimed in claim 11, wherein said solution is applied by thermonebulization.

14. The method as claimed in claim 11, wherein the solution is applied at a temperature of between 230 and 250° C.

15. A method for preparing a CIPC solution according to claim 1, said method comprising solubilizing the CIPC in the presence of the clove oil.

\* \* \* \* \*